(12) United States Patent
Resche-Rigon et al.

(10) Patent No.: US 9,814,732 B2
(45) Date of Patent: Nov. 14, 2017

(54) ULIPRISTAL ACETATE FOR PREVENTION AND TREATMENT OF BREAST TUMORS

(71) Applicants: LABORATOIRE HRA-PHARMA, Paris (FR); INSERM (Institut National de la Sante et de la Recherche Medicale), Paris (FR)

(72) Inventors: Michele Resche-Rigon, Paris (FR); Delphine Levy, Bagnolet (FR); Erin Gainer, Paris (FR); Anne Gompel, Paris (FR); Patricia Forgez, Palaiseau (FR); Laudine Desreumaux-Communal, Montreal (CA)

(73) Assignees: Laboratoire HRA-PHARMA, Paris (FR); INSERM (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 15/223,066

(22) Filed: Jul. 29, 2016

(65) Prior Publication Data
US 2017/0014426 A1 Jan. 19, 2017

Related U.S. Application Data

(63) Continuation of application No. 14/403,304, filed as application No. PCT/EP2013/060801 on May 24, 2013, now abandoned.

(30) Foreign Application Priority Data

May 25, 2012 (EP) .................................... 12305586

(51) Int. Cl.
*A61K 31/57* (2006.01)
*A61K 9/00* (2006.01)

(52) U.S. Cl.
CPC ............ *A61K 31/57* (2013.01); *A61K 9/0036* (2013.01); *A61K 9/0039* (2013.01); *A61K 9/0053* (2013.01)

(58) Field of Classification Search
CPC .................................. A61K 31/57; A61K 9/00
See application file for complete search history.

(56) References Cited

U.S. PATENT DOCUMENTS

2007/0213306 A1* 9/2007 Hausknecht ......... A61K 31/557
514/169
2012/0115831 A1* 5/2012 Hausknecht ......... A61K 31/557
514/179

FOREIGN PATENT DOCUMENTS

WO    WO2010066749    *  6/2010

OTHER PUBLICATIONS

Glasier et al. (The Lancet vol. 375 (2010)).*
Gudas et al. (Cancer Res. 55,4561-4565 1995).*
Katiyar et al. (Nuclear Receptor Signaling (2006) 4, e006).*
Poole et al. (Science 314, 2006).*
Hartman et al. (The New England J. Medicine (2005) 53(3).*

* cited by examiner

*Primary Examiner* — Shirley V Gembeh
(74) *Attorney, Agent, or Firm* — Leason Ellis LLP

(57) ABSTRACT

The invention relates to the use of ulipristal acetate, or any of its metabolites, in preventing or treating a breast tumor in a patient, preferably a patient that carries a mutation in BRCA1 gene.

**15 Claims, 8 Drawing Sheets
(2 of 8 Drawing Sheet(s) Filed in Color)**

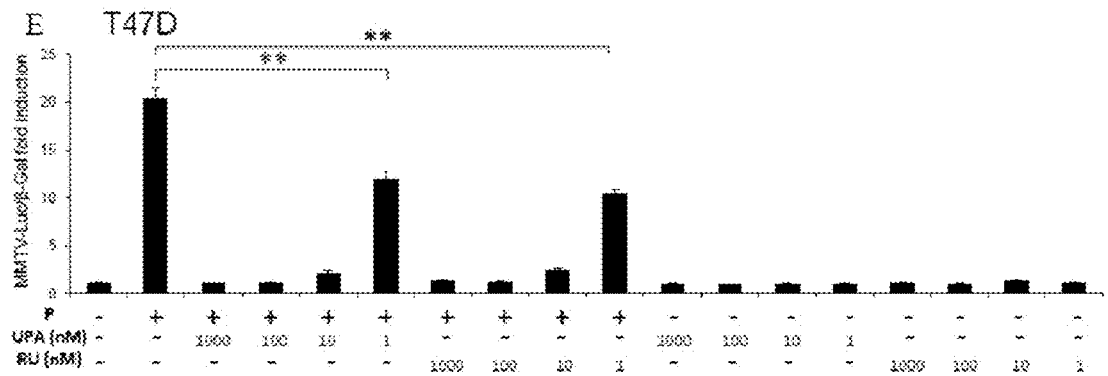
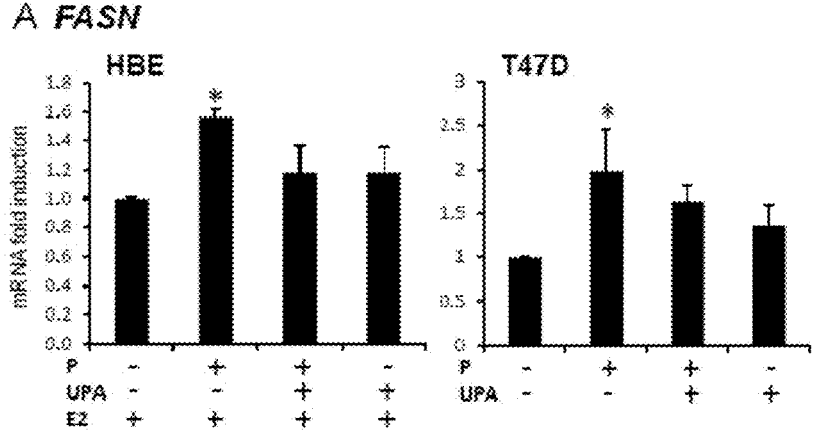
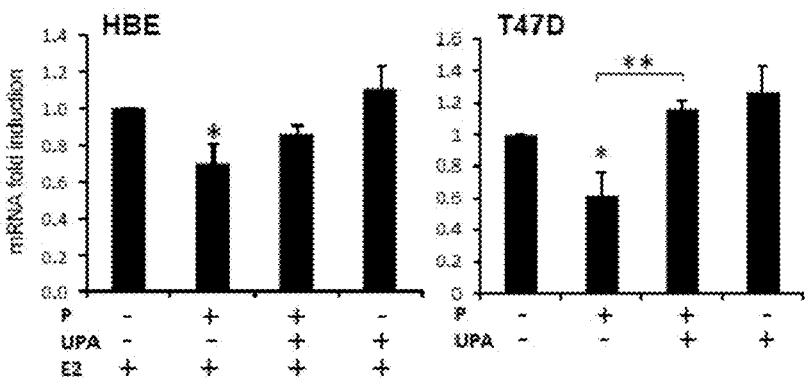
Figure 2

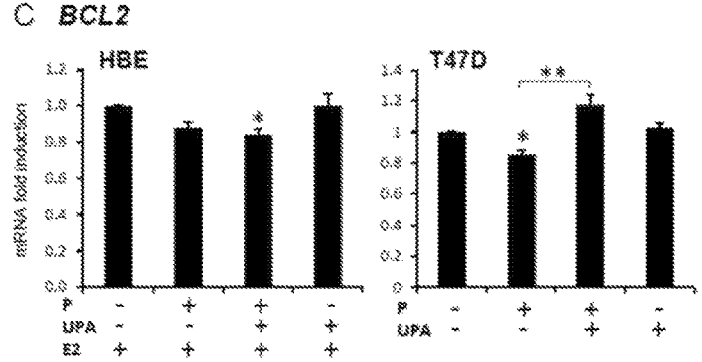
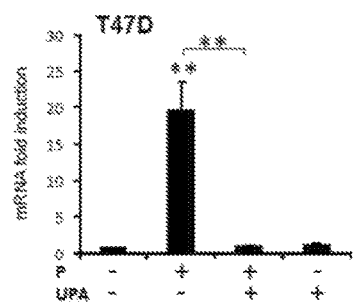
FIGURE 2 cont
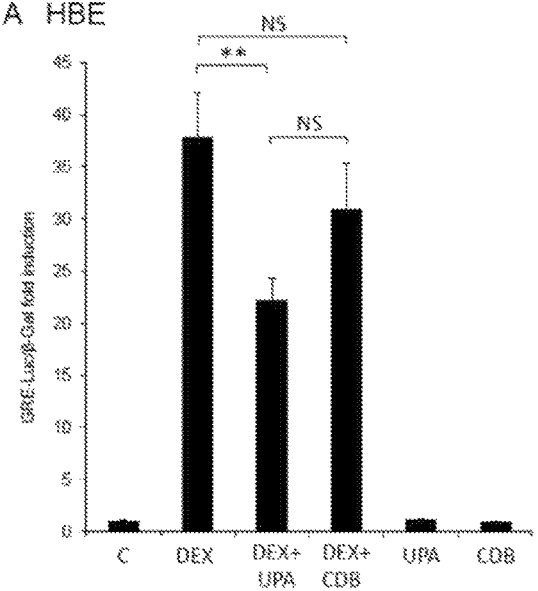
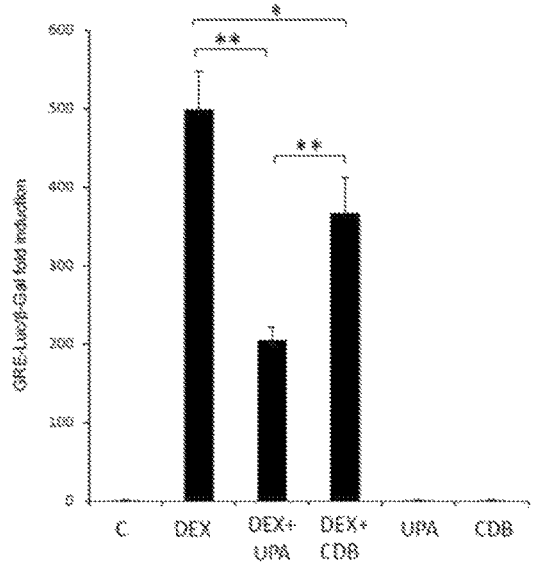
Figure 3

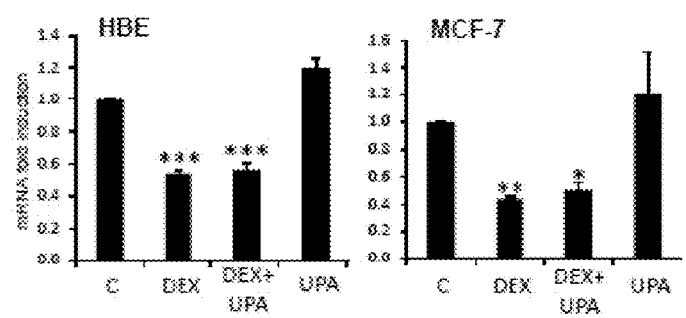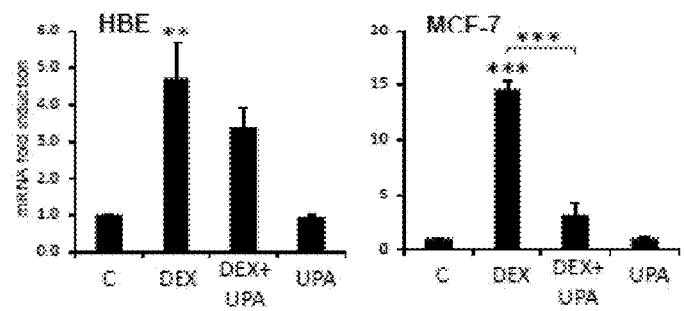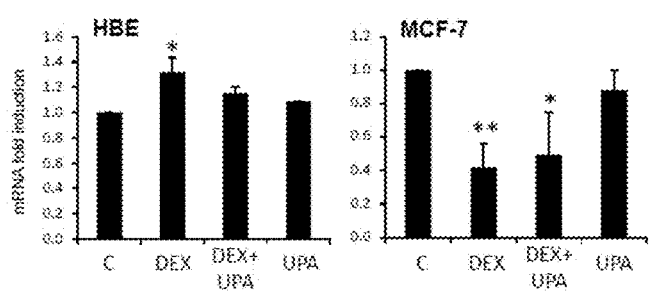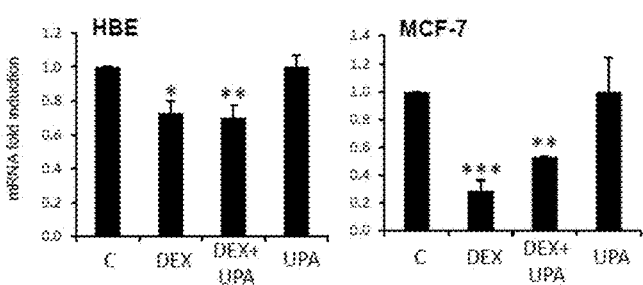
Figure 4

ULIPRISTAL ACETATE FOR PREVENTION AND TREATMENT OF BREAST TUMORS

The present invention relates to prevention and therapy of breast tumor with ulipristal acetate.

BACKGROUND OF THE INVENTION

Ulipristal acetate (UPA) is a progesterone receptor modulator which efficiently binds and inhibits progesterone receptor in progesterone target tissues.

UPA, formerly known as CDB-2914, designates 17□-acetoxy-11□-[4-N,N-dimethylamino-phenyl]-19-nor-pregna-4,9-diene-3,20-dione, represented by formula I:

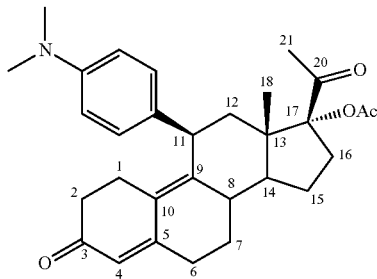

UPA, and methods for its preparation, are described e.g., in U.S. Pat. Nos. 4,954,490; 5,073,548; and 5,929,262, as well as in international patent applications WO2004/065405 and WO2004/078709.

UPA has been approved for emergency contraception (under tradename EllaOne®), and for treatment of uterine fibroids (under tradename Esmya®). Various other potential clinical applications have been proposed in Chabbert-Buffet et al, Human Reproduction, 2005, 11(3): 293-307.

Other antiprogestins such as mifepristone and onapristone were developed for breast cancer treatment. Administration of mifepristone or onapristone in a second or third line of treatment, in 123 postmenopausal women with metastatic breast cancers induced objective response rate and disease stabilization in 11% and 43% of the patients, respectively (Romieu et al. 1987, Bull Cancer 74(4): 455-461; Klijn, et al. 1989, Cancer Res 49(11): 2851-2856). Unfortunately, clinical studies were not sustained because of the anti-glucocorticoid and liver toxic side effects of mifepristone and onapristone, respectively.

Long term UPA exposure may affect hormone-responsive tissues, and particularly breast tissue, as well. However, only gene reporter transactivation studies in T-47D breast cancer cell line were reported (Attardi et al. 2002, Mol Cell Endocrinol 188(1-2): 111-123; Attardi et al. 2004, J Steroid Biochem Mol Biol 88(3): 277-288). There is still a need for a therapeutic agent for treating, and even preventing breast tumors, while causing no or reduced side-effects.

SUMMARY OF THE INVENTION

The inventors now propose a method for preventing or treating a breast tumor in a patient, which method comprises administering ulipristal acetate (UPA) or any of its metabolites.

It is therefore provided ulipristal acetate (UPA) or any of its metabolites for use in preventing or treating a breast tumor in a patient.

In a preferred embodiment, the patient carries a mutation in BRCA1 and/or BRCA2 gene.

In a particular preferred embodiment, ulipristal acetate (UPA) or any of its metabolites is used in preventing a breast tumor in a patient that carries a mutation in BRCA1 and/or BRCA2 gene.

In another preferred embodiment, ulipristal acetate (UPA) or any of its metabolites is used in treating a breast tumor in a patient, wherein the breast tumor preferably is a breast carcinoma.

DETAILED DESCRIPTION OF THE INVENTION

The "patient" means any subject in need of the preventive or curative treatment of the invention, preferably a woman. However men are also encompassed, since they may be susceptible to breast tumors as well.

Preferably the patient has been diagnosed to carry a mutation in BRCA1 and/or BRCA2 gene.

BRCA1 and BRCA2 are tumor suppressor genes.

The mutational events of the BRCA1 or BRCA2 locus can involve deletions, insertions, and point mutations within the coding sequence and the non-coding sequence. Deletions may be the entire gene or only a portion of the gene. Point mutations may result in stop codons, frameshift mutations, or amino acid substitutions. Somatic mutations are those which occur only in certain tissues, e.g., in the tumor tissue, and are not inherited in the germline. Germline mutations can be found in any of a body's tissues or cells and are inherited. If only a single allele is mutated, a predisposition to breast cancer is indicated.

In a particular embodiment, the patient may carry one copy or two copies of BRCA1 or BRCA2 predisposing alleles.

It is believed that BRCA1 or BRCA2 predisposing alleles are recessive to wild-type alleles; that is, cells that contain at least one wild-type BRCA1 or BRCA2 allele are not cancerous. However, cells that contain one wild-type BRCA1 or BRCA2 allele and one predisposing allele may occasionally suffer the loss of the wild-type allele, either by random mutation or by chromosome loss during cell division. All the progeny of such a mutant cell lack the wild-type function of BRCA1 or BRCA2 and may develop into tumors. Thus, the predisposing alleles of BRCA1 or BRCA2 are susceptible to cancer, and the susceptibility is inherited in a dominant fashion.

The majority of mutant alleles are nonsense or frameshift and produce truncated proteins which are predicted to vary in length from 5% to 99% of the full-length protein. Many of these mutations reside in exon 11 of BRCA1 gene which comprises 61% of the BRCA1 coding region. The full-length BRCA1 cDNA sequence and the coding regions of BRCA1 gene have been described in U.S. Pat. No. 5,747,282.

The mutations in BRCA1 or BRCA2 may be detected by any method known in the art.

Myriad's current BRCA diagnostic test, BRACAnalysis®, uses a combination of two traditional technologies—Sanger sequencing and PCR—to identify mutations associated with a significant risk of breast cancer in the BRCA1 and BRCA2 genes. Other methods for screening for BRCA1 and BRCA2 mutations include single stranded conformational polymorphism (SSCP) analysis and selected DNA sequencing of gene variants, or DHPLC and DNA sequencing of gene variants. Still other methods have been disclosed, including protein-based systems for detecting mutations in the BRCA1 gene (U.S. Pat. No. 5,965,377; U.S. Pat. No. 6,514,713).

The term "tumor" refers to the presence of cells possessing characteristics such as atypical growth or morphology, including uncontrolled proliferation, immortality, metastatic potential, rapid growth and proliferation rate, and certain characteristic morphological features. "Tumor" includes both benign and malignant (i.e. cancerous) neoplasms. Adenomas and cysts are encompassed. Breast cancers include breast carcinomas. Breast cancer can begin in different areas of the breast—the ducts, the lobules, or in some cases, the tissue in between. In the context of the present invention, any type of breast tumor or breast cancer is encompassed, including non-invasive, invasive, recurrent, and metastatic breast cancers.

In a particular embodiment, the patient has been diagnosed with a Hereditary Breast and Ovarian Cancer (HBOC).

It is herein described a preventive and a therapeutic method against breast tumor. "Prevention" or "preventing" means that UPA or any of its metabolites is administered in a patient who is asymptomatic or does not show a breast tumor. More particularly the patient may be at risk of developing such breast tumor, e.g. in view of the family history or of the BRCA1 and/or BRCA2 gene status. Such prevention aims at reducing the risk of developing a breast cancer.

"Therapeutic treatment" or "treating" means that UPA or any of its metabolites is administered in a patient who has been diagnosed with a breast tumor. The treatment alleviates the symptoms of the disease, slows down the progression of the disease, may lead to a remission or to a complete cure of the disease.

In particular, UPA was shown to antagonize the proliferation of tumor cells, in particular in lobules and galactophores (or ductal cells), in particular in BRCA1 mutant cells.

In a particular embodiment, the patient, who may be at risk of developing a breast tumor, but not necessarily, may be further in need of a contraception. This is particularly useful when the patient has no regular contraception. If so, UPA or any of its metabolites, may be proposed in a form and dosage adapted to provide both regular contraception and breast tumor prevention. In another embodiment, the patient may have uterine fibroids, and be both in need of a treatment against uterine fibroids and in need of a therapeutic or preventive treatment against a breast tumor. In that case, UPA or any of its metabolites, may also be proposed in a form and dosage adapted to provide both treatment against uterine fibroids and prevention or treatment of a breast tumor.

Ulipristal acetate (UPA) is preferably used. However metabolites of UPA could be used as well. Metabolites of ulipristal acetate, include those described in Attardi et al, Journal of Steroid Biochemistry & Molecular Biology, 2004, 88: 277-288, e.g. monodemethylated CDB-2914 (CDB-3877); didemethylated CDB-2914 (CDB-3963); 17alpha-hydroxy COB-2914 (CDB-3236); aromatic A-ring derivative of CDB-2914 (CDB-4183). Preferably the metabolite is monodemethylated CDB-2914 (CDB-3877).

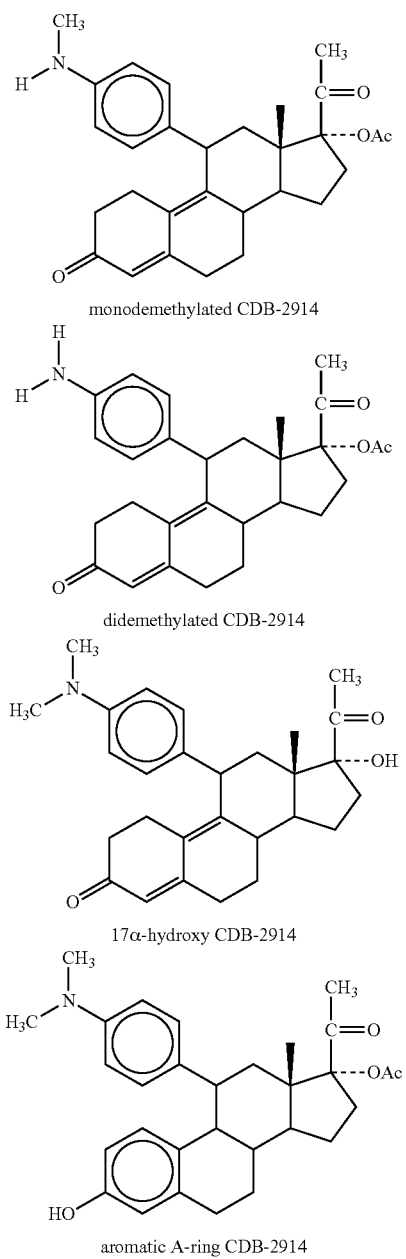

monodemethylated CDB-2914 didemethylated CDB-2914

17α-hydroxy CDB-2914 aromatic A-ring CDB-2914

UPA or its metabolites may be administered by various routes, e.g., orally, intravenously, or transdermally. A preferred administration route is the oral route. An injection at the site of the tumor is also possible. Other routes of administration are encompassed, including the vaginal or intrauterine route. Devices, in particular vaginal or intrauterine devices, allowing sustained release of UPA or its metabolites may be particularly useful. Subcutaneous implants may be further contemplated.

Methods and compositions for making useful dosage units are well-known to those skilled in the art. For example, conventional techniques for making tablets and pills, containing active ingredients, are described in the standard reference, Chase et al., Remington's Pharmaceutical Sciences, (16th ed., Mack Publishing Co., Easton. Pa., U.S.A., 1980) ("Remington's"), at pages 1553 through 1584. Conventional techniques for making powders, and their composition are described at pages 1535 through 1552 of the reference. Conventional techniques for coating pharmaceutical dosage forms are described at pages 1585 to 1593 of Remington's.

Oral solid dosage forms are preferentially compressed tablets, that may be coated or uncoated, or capsules.

Capsules are solid dosage forms using preferentially either a hard or soft gelatine shell as a container for the mixture of the active ingredient and inert ingredients. Procedures for production and manufacture of hard gelatin and soft elastic capsules are well known in the art.

Compressed tablets may contain any excipients which are diluents to increase the bulk of the active ingredient so that production of a compressed tablet of practical size is possible. Binders, which are agents which impart cohesive qualities to powdered materials are also necessary. Starch, gelatine, sugars such as lactose or dextrose, and natural and synthetic gums are used. Disintegrants are necessary in the tablets to facilitate break-up of the tablet. Disintegrants include starches, clays, celluloses, algins, gums and cross-linked polymers. Lastly small amounts of materials known as lubricants and glidants are included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Procedures for the production and manufacture of compressed tablets are well known by those skilled in the art.

In a particular embodiment, ulipristal acetate or a metabolite thereof is used in form of an uncoated tablet wherein ulipristal acetate or a metabolite thereof is mixed with excipients that are lactose monohydrate, povidone (polyvinylpyrolidone), croscarmellose sodium, and magnesium stearate (e.g. as described in international patent application WO2010/066749).

Long term treatments are preferred, e.g. for a period of at least 3 months.

In the context of prevention, the treatment may be maintained several years.

In the context of a curative treatment, UPA may be administered from a few days, to several months or years, e.g. during at least 3 months to about 5 years.

Dosage may be adapted depending on the specific condition and severity of the tumor, and the gender and weight of the patient. A typical dosage would range from 0.1 mg to 150 mg, preferably between 5 and 80 mg, still preferably between 10 and 50 mg. Daily administration(s) are preferred.

The examples and figures illustrate the invention without reducing its scope.

MMTV-Luc reporter gene was transfected in HBE cells: (A) alone, or in combination, (B) with hPR-A and hPR-B, (C) hPR-A, or (D) hPR-B isoform plasmids. (E) T-47D cells were transfected with MMTV-Luc. Cells were treated with P at 100 nM and/or UPA, or RU from 1 to 1 000 nM as indicated or with 100 nM when not specified. Results correspond to control fold induction (mean±SEM, n=3 for HBE and T-47D). *p<0.05, **p<0.001.

FIG. 2: UPA effects on PR target gene expression.

11 In HBE and T-47D cells, mRNA expression was analyzed by Quantitative RT-PCR for (A) FASN, (B) cyclin A, (C) BCL2 and (D) ALPL. Cells were treated with P and/or UPA at 100 nM, and/or E2 at 10 nM. Results correspond to control fold induction (mean±SEM, n=5 for HBE and n=2 for T47D). *p<0.05, **p<0.01.

FIG. 3: UPA effects on GRE reporter gene transactivation.

GRE-Luc reporter gene was transfected in (A) HBE cells and in (B) MCF-7 cells. Cells were treated by DEX and/or UPA at 100 nM. Results correspond to control fold induction (mean±SEM, n=13 for HBE and n=3 for MCF-7). *p<0.01, **p<0.001.

FIG. 4: UPA effects on GR target gene expression.

In HBE and MCF-7 cells, mRNA expression was analyzed by Quantitative RT-PCR for (A) IEX-1, (B) G0S8, (C) cyclin A, (D) BCL2. Cells were treated with DEX and/or UPA at 100 nM. Results correspond to control fold induction (mean±SEM, n=5 for HBE and n=2 for MCF-7). *p<0.05, p<0.01, *p<0.001.

Figure 5:
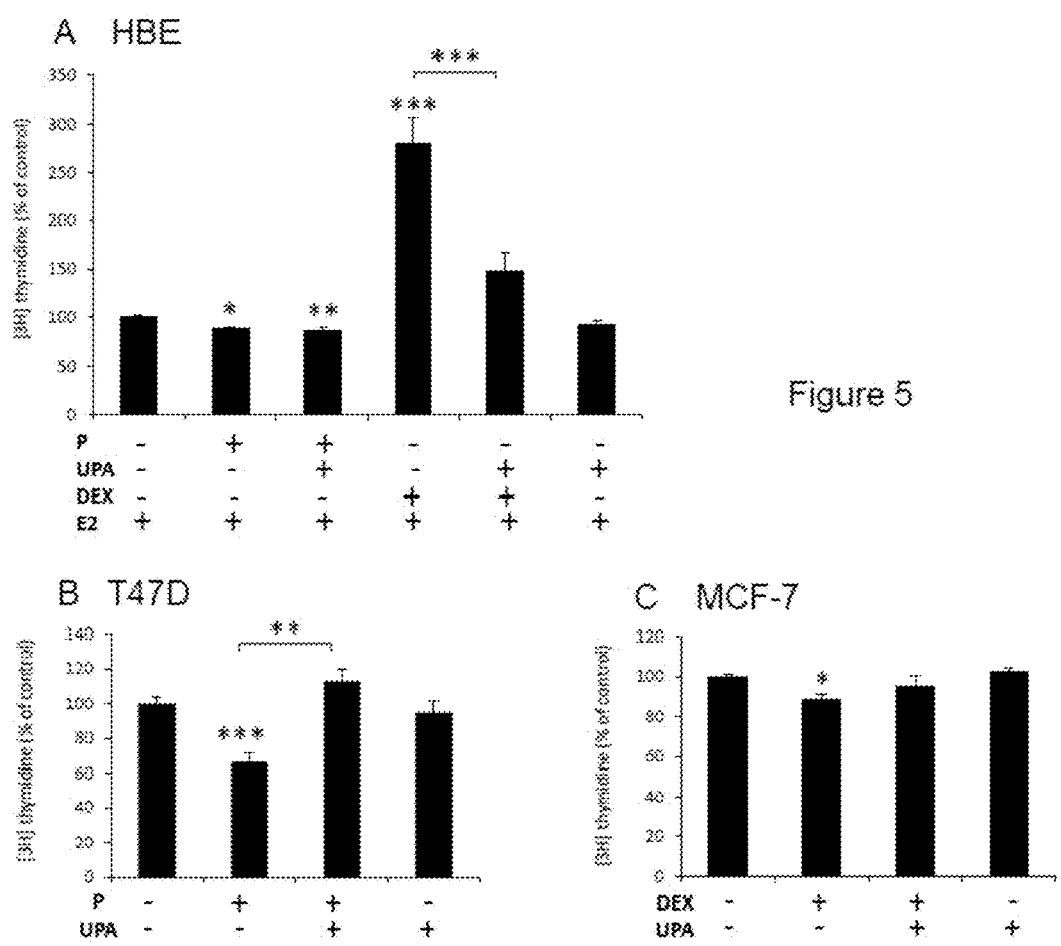

FIG. 5: UPA effect on hormone mediated cell 1 proliferation.

Cell proliferation was measured by [3H] thymidine incorporation in (A) HBE cells, (B) T47D cells and (C) MCF-7 cells. HBE cells were treated 96 h and T-47D and MCF-7 cells were treated 48 h at the concentration of 100 nM for P, DEX, UPA and 10 nM for E2. Results are expressed in percentage of control (mean±SEM, n=7 for HBE, n=4 for T47D and n=3 for MCF-7). *p<0.05, p<0.01, *p<0.001.

Figure 6:
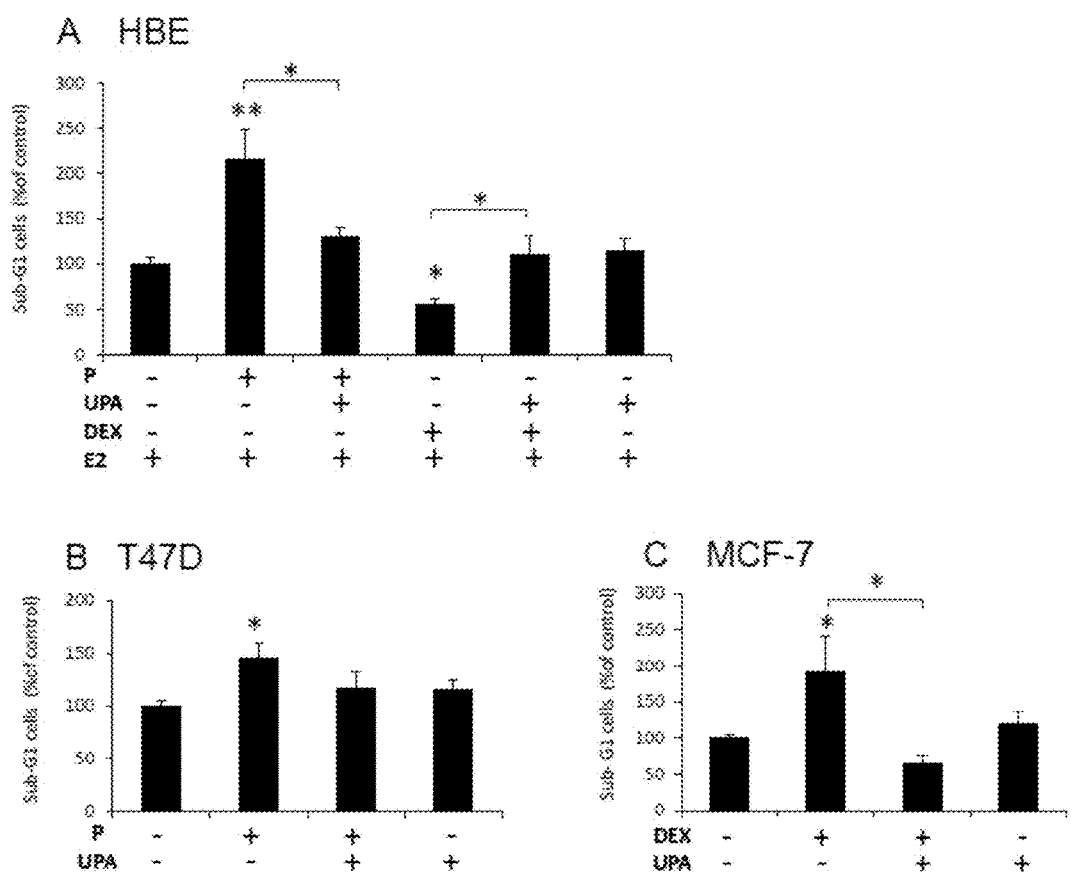

FIG. 6: UPA effects on hormone mediated cell apoptosis.

Cell apoptosis was measured by flow cytometry quantification of sub-G1 phase in (A) HBE cells, (B) T-47D cells, and (C) MCF-7 cells. HBE cells were treated 96 h and T-47D and MCF-7 cells were treated 48 h at the concentration of 100 nM for P, DEX, UPA and 10 nM for E2. Results are expressed in percentage of control (mean±SEM, n=9 for HBE, n=3 for T-47D and n=4 for MCF-7). *p<0.05, **p<0.001.

Figure 7:
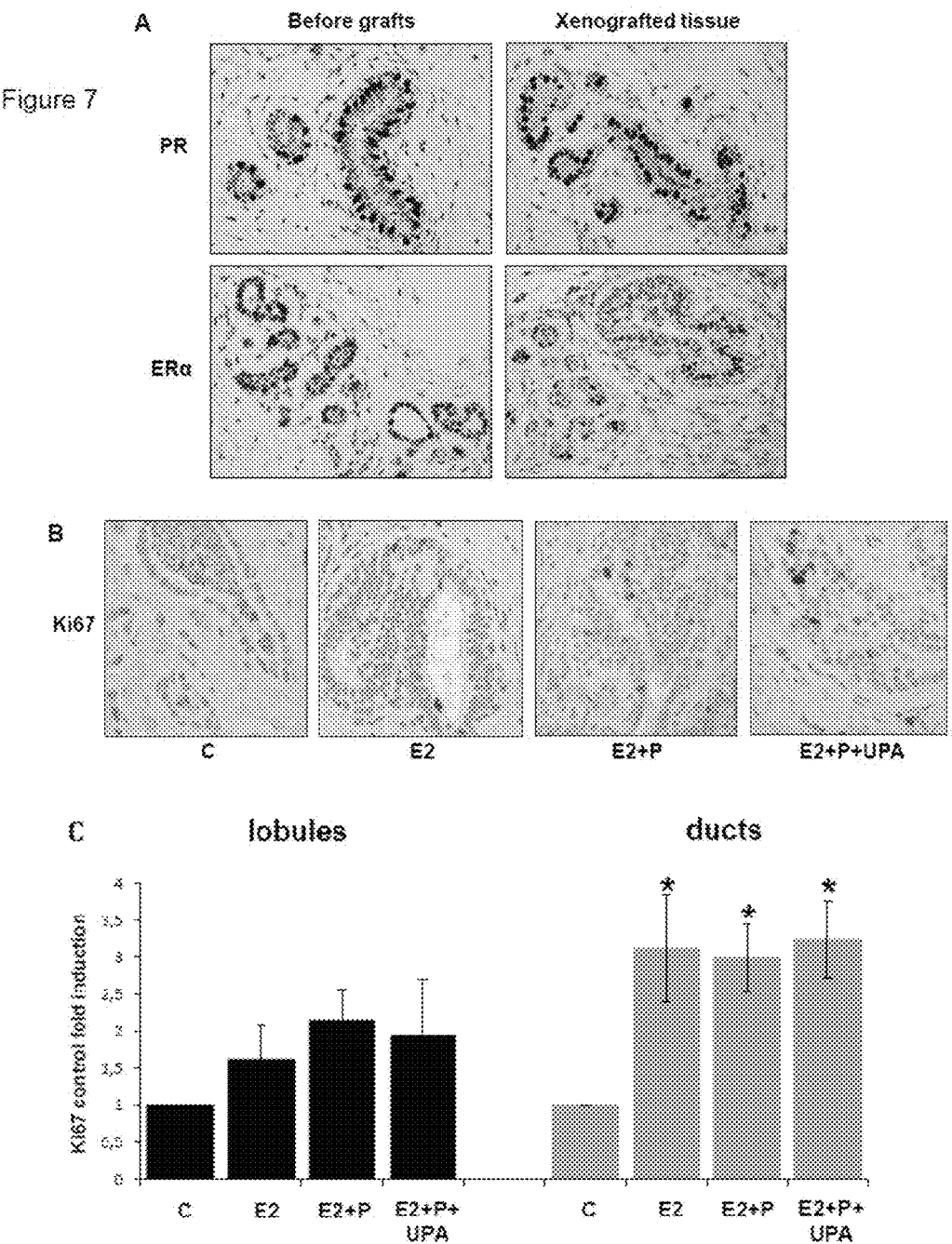

FIG. 7: PR, ER and Ki67 expressions in breast tissue xenografts.

ER, PR and Ki67 expression were analyzed by immunohistochemistry. (A) Representative image for ER and PR labeling in original breast tissue before and in treated grafts in mice. (B) Ki67 expression in C, E2, E2+P, E2+P+UPA treatment groups of grafted tissues. Magnification ×400. (C) Mitotic index (Ki67 positive cells percentage) control fold induction in lobules and ducts (mean±SEM, n=4 in lobules and n=6 in ducts). *p<0.05.

Figure 8:
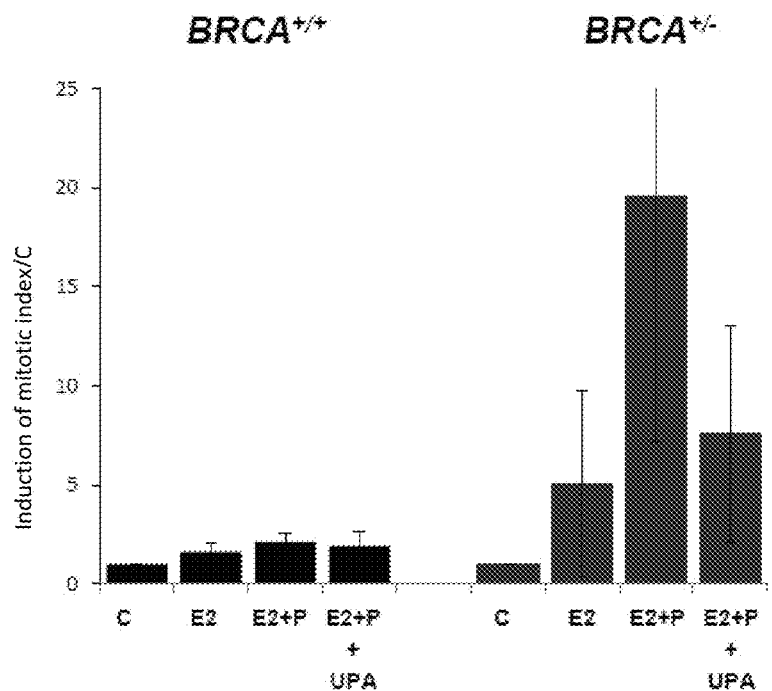

FIG. 8 shows induction of mitotic index (Ki67 positive cells percentage) in lobular cells of grafted tissues that carry BRCA1 mutations (BRCA1$^{+/+}$) or not (BRCA1$^{+/-}$), in response to various treatments. mean±SEM.

Figure 9:
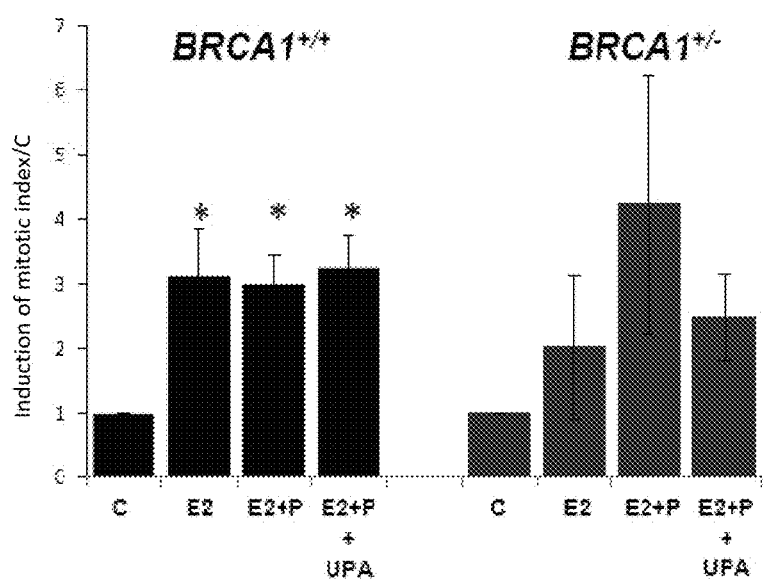

FIG. 9 shows induction of mitotic index (Ki67 positive cells percentage) in ductal cells of grafted tissues that carry BRCA1 mutations (BRCA1$^{+/+}$) or not (BRCA1$^{+/-}$), in response to various treatments. mean±SEM.

EXAMPLES

Example 1

Impact of UPA on Proliferation and Apoptosis of Normal Breast Epithelial Cells (HBE) and in Breast Cancer Cell Lines Materials and Methods Steroids The progesterone receptor antagonist ulipristal acetate (UPA) and its mono-N4 demethylated metabolite CDB-3877

(CDB) were kindly provided by HRA-Pharma (Paris, France). 17β estradiol (E2), progesterone (P), dexamethasone (DEX) and mifepristone/RU-486 (RU) were purchased from Sigma (St Quentin Fallavier, France).

Cell Culture Procedures

T-47D and MCF-7 cell lines were respectively maintained in RPMI 1640 and in DMEM medium supplemented with 10% fetal calf serum (PAA Laboratory, Les Mureaux, France). T-47D cell line was derived from a human ductal breast carcinoma and constitutively expressed high amounts of PR (progesterone receptor) and ER (estradiol receptor). Normal human breast epithelial cell (HBE) primary cultures were obtained from 20 women (aged 17-50 years). The procedure used to culture HBE cells is described in detail by Gompel and colleagues (Gompel, et al., 1986, J Clin Endocrinol Metab 63(5): 1174-1180). HBE cells were maintained in HAM F10 medium (PAA Laboratory, Les Mureaux, France) containing hydrocortisone (5 ng/ml), Triiodo-L-thyronine (6.5 ng/ml), choleratoxin (10 ng/ml), transferrin (5 mg/ml), insulin (0.016 U/ml), epidermal growth factor (10 ng/ml) (Sigma, St Quentin Fallavier, France) and 5% human serum (Etablissement Français du Sang). HBE primary cultures express epithelial markers as well as low levels of estradiol receptor (ER) and estradiol induced PR (Malet, et al., 1991. J Clin Endocrinol Metab 73(1): 8-17; Courtin, et al., 2011, Breast Cancer Res Treat.).

Steroid Treatments

After seeding, cells were cultured for 24 h in serum and phenol red free medium. Then treatments were carried out in a phenol red free medium containing 5% dextran-charcoal stripped serum. Cells were treated with P or DEX (100 nM), alone or in combination with UPA, RU (1 nM to 1 µM) or CDB-3877 (100 nM). Control cells were treated with ethanol, at 10 1:1000 final ethanol concentration alone as vehicle or E2 (10 nM).

Reporter Enzyme Assays

Cells were transfected with reporter gene plasmids containing glucocorticoid and progesterone responsive elements (GRE/PRE): 1) the MMTV-Luc is a Mouse Mammary Tumor Virus Long Terminal Repeat promoter containing one GRE/PRE palindrome and three GRE/PRE hemi-palindromes upstream to firefly luciferase gene in pFC31 vector, 2) the GRELuc contains six copies of GRE/PRE palindrome upstream to firefly luciferase gene in pBL vector. When indicated, HBE cells were transfected with human PR isoforms hPR-A and hPR-B expression plasmids constructed in POP3 vectors. Rous Sarcoma Virus promoter upstream to beta galactosidase gene (pRSV-β-Gal) was transfected in each experiment as control. Transfections were performed according to the manufacturer instructions using Lipofectamine or Lipofectamine LTX Reagents (Invitrogen, Cergy-Pontoise, France) for breast cancer cell lines or HBE cells, respectively. After 24 h of transfection, breast cancer and HBE cells were treated with hormones for 24 h or 48 h, respectively. At the end of the experiment, cells were lysed and luciferase activity was determined using the Luciferase Assay System (Promega, Charbonnières-les-bains, France). Beta galactosidase activity was assessed using the Galacto Star kit (Applied Biosystems, Courtaboeuf, France) to normalize luciferase activity data.

Real-Time Quantitative Reverse Transcription PCR (qRT-PCR)

Total RNA was extracted using TriZOL Reagent (Invitrogen, Cergy-Pontoise, France).

2 µg of total RNA was subjected to reverse transcription (RT) using random primers for 1 h at 37° C. 2 µl of RT product was diluted (1:10) and subjected to quantitative PCR using sequence specific primers (300 nM) and Brillant SYBR GREEN QPCR master mix (Fermentas, Saint-Rémy-lès-Chevreuse, France) on an Mx3000P apparatus (Agilent Technologies, Massy, France). Conditions were 1 cycle at 95° C. for 10 min followed by 40 cycles at 95° C. for 30 sec, 60° C. for 1 min and 72° C. for 30 sec. Gene expression values were normalized to the housekeeping gene 36B4. Time of steroid treatment was chosen to get the optimal stimulation for a given gene. ALPL and G0S8 mRNA were analyzed after 6 h of treatment. IEX-1, FASN, and BCL2 were analyzed after 24 h of treatment. Cyclin A mRNA was analyzed after 24 h for GR responses or 48 h for PR responses.

Tritiated Thymidine Incorporation

After 24 h of hormonal treatment, cells were incubated with [methyl-1 3H] thymidine (Perkin Elmer, Courtaboeuf, France) for 48 h or 20 h for KBE or cancer cells, respectively at 37° C. After incubation cells were washed twice with PBS 1× and once with 5% trichloroacetic acid (TCA). Cells were incubated in 5% TCA for 15 min at 4° C. and lysed in NaOH 0.1 N for 30 min at 37° C. The total cell lysate was added to 5 ml of Ecolite scintillation liquid (MP biomedical, Illkirch, France) and radioactivity was counted with a β-counter HIDEX 300SL (ScienceTec, Courtaboeuf, France).

Flow Cytometry Analysis

After 96 h or 48 h of hormonal treatment, respectively, for HBE or MCF-7 and T-47D cells, cells were washed in PBS, matrix dissociated with accutase enzyme (PAA laboratory, Les Mureaux, France), and centrifuged 5 minutes at 1350 rpm. Cells were fixed and frozen at −20° C. in 70% ethanol. Before analysis, cells were washed in PBS and stained with 10 µg/ml propidium iodide in PBS (containing 0.835 U/ml RNase A) (Sigma, St Quentin Fallavier, France). For each sample at least 10 000 cells were counted in a BD LSR II flow cytometer (BD Biosciences, Le Pont de Claix, France). After gating out doublets and debris, cycle distribution was analyzed using the ModFit LT software (Verity Software House, USA).

Statistical Analysis

Results were expressed in mean±SEM. To determine the statistical significance of treatments, One-way ANOVA and Tukey-Kramer multiple comparisons tests were performed to compare the relative efficiency of each treatment with the Instat 3 software (GraphPad, USA). When only two treatments were compared, an unpaired t test was performed. $p<0.05$ was considered as significant.

Results

UPA Effects on PR Gene Transactivation

Figure 1:
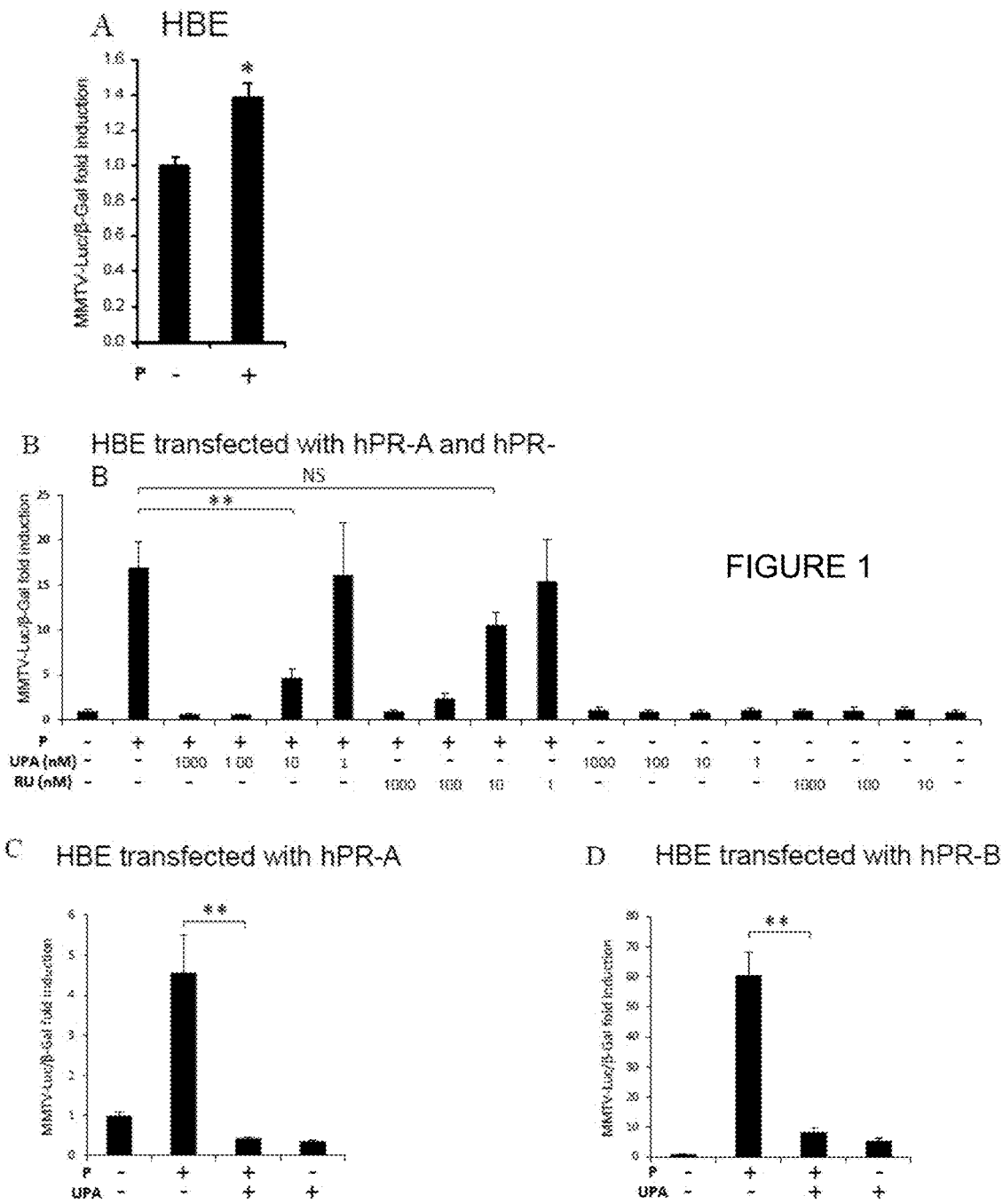
FIG. 1: UPA effects on MMTV reporter gene transactivation.

In order to analyze UPA antagonist properties on PR-induced gene transactivation, normal human breast epithelial cells (HBE) and T-47D breast cancer cell line were transfected with the MMTV-Luc reporter gene (FIG. 1). In HBE cells which expressed low and variable amounts of PR among patients (Malet, et al., 1991. J Clin Endocrinol Metab 73(1): 8-17), progesterone (P) induced a significant luciferase expression (1.38±0.11 control fold induction, $p<0.05$) (FIG. 1 A). To better study the dose effects of UPA on PR, HBE cells were co-transfected with hPR-A and hPR-B expression plasmids (FIG. 1 B). UPA and RU-486 (RU) inhibited P induced MMTV11 Luc transactivation in a dose dependent manner from 1 000 to 10 nM. HBE cells were then also transfected with only hPR-A or hPR-B, to discriminate UPA actions between PR isoforms. No difference with increasing the levels of each PR isoform was seen on UPA antagonist performance (FIG. 1 C, D). In the T-47D cell line, UPA and RU displayed similar and potent PR antagonist actions from 1000 to 10 nM (FIG. 1 E). Partial antagonist responses were also detected at 1 nM (FIG. 1 E). In both HBE and T-47D cells, UPA and RU did not exhibit progestational agonist properties on reporter gene transcription (FIG. 1 B-E). These results indicated that UPA acted as a potent P antagonist in normal and cancerous breast cells.

UPA Activity on mRNA Expression of PR Target Genes

A hundred nM was the lowest concentration of UPA necessary to exert a complete antagonist activity in HBE cells. This concentration was therefore, chosen to further study the effects of UPA on specific P target genes in HBE and T-47D cells. Estradiol (E2) was added to HBE cells, in order to increase PR expression as reported previously.

Fatty acid synthase (FASN) is implicated in normal breast cells differentiation as well as in mammary tumor progression. An up3 regulation of FASN mRNA by progestins through PR was previously demonstrated in normal and tumoral breast cells in vitro and in vivo. As shown in FIG. 2 A, UPA was able to prevent P induction of FASN mRNA expression in HBE as in T-47D cells. We observed that P down regulated cyclin A mRNA expression in normal breast cells and in T-47-D cells (FIG. 2 B), as previously reported in MDA-MB-231 breast cancer cells transfected by PR (Lin, et al., 2003, Endocrinology 144(12): 5650-5657.). UPA reversed P-induced cyclin A mRNA down-regulation in HBE and T-47D (FIG. 2 B). We previously reported a decrease of the anti-apoptotic B-cell CLL/lymphoma 2 (BCL2) protein expression under progestin treatment in normal and tumoral breast cells (Kandouz, et al., 1996, Int J Cancer 68(1): 120-125; Gompel, et al., 2000, Steroids 65(10-11): 593-598). As shown in FIG. 2 C, we also observed a decrease of BCL2 mRNA expression by P in HBE and T-47D cells.

Nevertheless, UPA did not reverse BCL2 mRNA down-regulation induced by P in HBE cells, whereas UPA antagonized the P inhibitory effect on this transcript in T-47D cells (p<0.01) (FIG. 2 C). Tissue non-specific alkaline phosphatase (ALPL) is a P responsive gene implicated in metastasis of breast cancer. In T-47D, UPA totally inhibited the strong P mediated induction of ALPL transcript (FIG. 2 D). In HBE cells, ALPL mRNA expression was not modified by P treatment (data not shown). UPA did not display any PR agonist activity on these genes.

UPA Effects on GR Gene Transactivation

The study was performed in HBE and MCF-7 cells, which expressed high amounts of GR as previously reported (Courtin, et al.; 2011, Breast Cancer Res Treat.). Cells were transfected with a GRE-Luc reporter gene and treated with dexamethasone (DEX), UPA, and its proximal mono-demethylated metabolite, CDB-3877 (CDB), known to exert less anti-glucocorticoid activity than UPA (Attardi, et al., 2004, J Steroid Biochem Mol Biol 88(3): 277-288.). We confirmed the reduced anti glucocorticoid activity of this metabolite, since UPA inhibited by 41.3±5.8% the DEX induced luciferase transactivation, whereas its metabolite failed to inhibit DEX activity in HBE cells (18.1±11.8%) (FIG. 3 A). However, in MCF-7 cells, both UPA and CDB significantly antagonized by 59±3.4% and 26.5±9.1, respectively, the DEX-induced luciferase transactivation (FIG. 3 B). These results suggest a stronger anti-glucocorticoid potency of UPA in MCF-7 breast cancer cells than in HBE.

UPA Activity on mRNA Expression of GR Target Genes

In order to better define UPA anti-glucocorticoid effects in HBE and MCF-7 cells, mRNA expressions of various glucocorticoid responsive genes were analyzed after DEX and UPA treatment. Immediate early response 3 (IEX-1) and regulator of G-protein signaling 2 (G0S8) have been implicated in cell survival under stress conditions and in G-protein signaling, respectively. IEX-1 and G0S8 were characterized as glucocorticoid responsive genes. As shown in FIG. 4 A, IEX-1 mRNA expression was down-regulated by DEX and UPA did not antagonize this response in HBE and MCF-7 cells. On the other hand, UPA exerted a slight and non-significant antagonist effect on DEX-induced up-regulation of G0S8 mRNA in HBE cells, whereas its anti-glucocorticoid activity was strong in MCF-7 cells (p<0.001) (FIG. 4 B). Cyclin A and BCL2 genes were previously shown to be regulated 1 by DEX in vitro in osteoblasts and neuroblastomas, respectively. DEX and UPA actions were therefore analyzed on cyclin A and BCL2 mRNA expression in HBE and MCF-7 cells. Cyclin A was differentially regulated by DEX in the two types of cells as mRNA expression was induced in HBE cells and repressed in MCF-7 cells (FIG. 4 C) (Courtin, et al.; 2011, Breast Cancer Res Treat.). In both cellular models, UPA partially inhibited DEX effect on cyclin A mRNA expression. BCL2 mRNA was down-regulated by DEX in HBE and in MCF-7 cells (FIG. 4 D). However, UPA did not reverse the DEX down-regulation of BCL2 mRNA in HBE cells, whereas it partially antagonized this effect in MCF-7 cells. UPA did not display any glucocorticoid agonist activity on these genes (FIG. 4).

UPA Action on Proliferation and Apoptosis

P and glucocorticoid can induce different proliferative and survival effects on normal and tumoral breast cells. In order to evaluate the role of UPA on these cellular events, proliferation and apoptosis were measured respectively by tritiated thymidine incorporation (FIG. 5) and flow cytometry (FIG. 6) in the three cellular models. UPA effects on PR were studied in HBE and T-47D, but not in MCF-7 cells, because we previously demonstrated a lack of PR functionality in this cell line (Courtin, et al.; 2011, Breast Cancer Res Treat.). UPA actions on GR were only studied in HBE and MCF-7 cells as T-47D cells used herein do not express GR (Courtin, et al.; 2011, Breast Cancer Res Treat.). In HBE cells, UPA did not inhibit the anti-proliferative effect induced by P (FIG. 5 A). Conversely, UPA inhibited the strong proliferative activity induced by DEX (FIG. 5 A). In T-47D cells, UPA reversed P anti-proliferative activity (FIG. 5 B). In MCF-7 cells, UPA tended to prevent the weak anti-proliferative effects of DEX (FIG. 5 C). UPA treatment alone had no effect on proliferation in any type of cells (FIG. 5). Apoptosis was measured by quantification of sub-G1 percentage 1 of cells by flow cytometry analysis. P exerted an intense pro-apoptotic effect in HBE cells, in contrast to DEX which displayed anti-apoptotic features (FIG. 6 A). When combined with UPA, both hormones activities were reversed. Similarly, P increased the percentage of sub-G1 cells and UPA tended to inhibit this effect in T-47D cells (FIG. 6 B). In MCF-7, DEX showed a pro-apoptotic ability which was totally inhibited by UPA (FIG. 6 C). UPA had no apoptotic or survival properties by itself, but counteracted most of the P and DEX effects in HBE, T-47D, and MCF-7 cells.

Example 2

Impact of UPA on an In Vivo Experimental Model, with Normal Human Breast Tissues Xenografted in the Nude Mice Materials and Methods Patients Breast tissues samples were obtained from 6 women (aged 29-42 years) undergoing surgery for reduction mammoplasty, with their informed consent according to the French law on clinical experimentation. The patients had no history of breast disease and immunohistochemical studies including a hematoxylin-phloxine-saffron (HPS) stain only showed normal breast tissue.

Human Breast Xenografts in Mice and Pellet Treatments

Four weeks old ovariectomized female NMRInu/nu athymic mice were purchased from Janvier laboratory (Le Genest Saint Isle, France). Breast tissues samples were obtained from 6 women (aged 29-42 years). Human mammary gland tissue was cut into 2×2×2 mm fragments and 4 fragments were then subcutaneously xenografted onto the back of 4 mice per group. Four treatment groups were performed: control, E2, E2+P and E2+P+UPA. Treatments were administered by grafting steroid pellets onto the neck of each mouse. The experimental conditions were initially determined by using a dose range of hormones mixed with cholesterol into the pellets. Blood sample assays were performed after 2 weeks and 4 weeks of treatment to measure plasmatic hormonal concentrations. Finally, the dose of 0.3 mg for E2 and 20 mg for P and UPA were used, as it provides the expected blood concentrations. For the control groups, pellets containing only cholesterol were used. To reproduce menstrual cycle conditions, mice were grafted on the first day of experiment with cholesterol, E2 and/or UPA containing pellets and on the fourteen day with cholesterol or progesterone containing pellets in control and E2 groups, or in E+P and E2+P+UPA groups, respectively. Twenty eight days after the start of experiment, mice were sacrificed. Blood was collected for each mouse, and serum was frozen at −20° C. until hormone concentrations Analyses.

Breast tissue fragments were collected and immediately fixed in paraformaldehyde solution for immunohistochemical analysis. All study protocols and environmental conditions of the animal rooms were approved by the French Ethic committee for the care and use of laboratory animals Charles Darwin.

Hormone Concentration Analysis

Estradiol was measured by radioimmunoassay using Clinical Assays Estradiol-2 (Sorin Biomedica Diagnostics SpA, Saluggia, Italia). Progesterone levels were evaluated by UPLC-MSMS using Acquity UPLC and Quattro Premier XE (Waters, Milford Mass., USA).

UPA concentrations were measured using LC-MS/MS technique by MPI Research (State College, Pa., USA).

Immunohistochemical Analysis

Mitotic index was calculated using the Ki67 antibody, and was determined for each breast tissue grafted into mice. Immunohistochemical analyses were performed using the BOND-MAX workstation (Leica, Nanterre, France). Paraffin sections of breast tissue xenografts were de-waxed and rehydrated before antigen retrieval using citrate retrieval solution (pH 6.0) for Ki67 antibody or EDTA retrieval solution (pH 9.0) for PR and ERalpha antibodies, for 30 min. Sections were then incubated with Ki67 at 1:100 (Novocastra, NCL5 L-Ki67-MM1), PR at 1:80 (Biogenex, MU-328-UC) or ER at 1:300 (Novocastra, NCL-L6 ER-6F11) monoclonal antibodies. For signal detection, the Kit Bond Polymer Refire Detection was used. Reagents were purchased from Menarini-Diagnostic (Rungis, France). A negative control (omitting the first antibody) was included in each set. For each marker, determination of the ratio of positive cells was performed on a total of 1 000 lobular and 1 000 ductal luminal cells in the 4 breast tissue fragments grafted into each mouse. For each experiment, the final percentages for each treatment were the mean of percentages obtained in the four mice per group.

Results

UPA Action on Breast Tissue Proliferation

The inventors developed an in vivo model to study UPA in long term administration on breast tissue. Human normal breast tissues samples were xenografted in athymic mice treated with E2, or E2+P, or E2+P+UPA, or cholesterol (control) (see experimental procedure). In order to reproduce the chronology of E2 and P secretions occurring in human female menstrual cycle, E2 pellets were grafted at the beginning of the experiment, whereas P pellets were grafted at the fourteenth day. UPA pellets were grafted at the beginning of the experiment to mimic a chronic treatment. E2, P, and UPA concentrations in mice serum were measured to validate the treatment method. Average E2 concentrations in mice serum was $36.88 \pm 4.25$ pg/ml (mean±SEM) corresponding to the low range of the physiological E2 levels reported in follicular phase. The P level was $13.05 \pm 1.14$ ng/ml (mean±SEM) equivalently to the average P plasma levels in women during the mid-luteal phase. UPA concentration was $63.49 \pm 10.46$ ng/ml (mean±SEM) in the same range that observed in clinical use. Hormones levels were undetectable in control mice (E2<0.8 pg/ml; P<0.4 ng/ml; UPA<0.5 ng/ml). As shown in FIG. 7 A, estradiol receptor (ER) and PR expressions were maintained in the treated engrafted breast fragments at the end of the experiment compared to the original breast tissue before grafts. We analyzed the mitotic Ki67 expression marker in order to determine the breast tissue proliferative activity in glandular lobules and ducts according to the treatment (FIG. 7 B, C). In the control group of grafted tissues, the rate of mitotic cells was low and homogeneous, at $1.7 \pm 0.4\%$ in the lobules and $1.8 \pm 0.6\%$ in ducts. The proliferative activity was slightly but not significantly increased in lobules of E2 treated group when compared to the control group (FIG. 7 B, C). However, in ducts, the mitotic index was significantly elevated in E2 treated group ($3.1 \pm 0.7$ fold induction compared to the control group, $p<0.05$). No significant difference was observed in E2+P and E2+P+UPA groups compared to E2 treatment in lobular and ductal structures (FIG. 7 B, C). These results strongly suggest that proliferative activity in breast tissue is predominantly mediated by E2. We also showed that UPA does not significantly influence the proliferation rate of normal epithelial breast cells.

Example 3

Impact of UPA on BRCA1 Human Breast Tissues Xenografted on Nude Mice

Materials and Methods

Mutated breast tissue samples were obtained from 5 women (36-57 years old) carrying mutations for BRCA1.

Xenografts were performed as described above (Example 2). Usually, 4 breast tissue fragments from a patient not carrying BRCA1 mutations and 4 breast fragments from a patient carrying BRCA1 mutations were grafted in the same mouse, on the left and right part of the spine respectively. The same groups were formed.

Results

The inventors used the same model as described in the above section to investigate the effects of hormones on the proliferation of human breast tissue collected in patient carrying BRCA1 mutations. A higher variability regarding ER□ expression was observed in both lobular and ductal structures of patients with BRCA1 mutations before being grafted. The basal expression level of PR was lower in patients carrying BRCA1 mutation compared to patients with a wild type allele in the lobular structures. In contrast the BRCA1 status did not impact PR expression level in ductal structures. The proliferative status measure through the expression of Ki67 was higher in lobular cells from BRCA1 patients, but lower in the ductal cells, compared to wild type patients.

After the graft, but in the absence of treatment, no significant statistical modification of ER□ expression was observed, whilst PR expression level in both lobular and ductal structures tended to be even lower than before the graft. In both structures the absence of hormonal stimulation resulted in decreased proliferation.

28 days treatment with E2, P, E2+P or E2+P+UPA did not result in significant variation of ER□ expression level. Trends towards increased PR expression were observed in breast fragments grafted in mice receiving either E2, or E2+P or E2+P+UPA. This increase was more particularly observed in the lobular structures of 3 patients carrying the BRCA1 mutation.

In each case where proliferation was stimulated by the combination of E2+P treatment, UPA exhibited antiproliferative activity (See FIGS. 8 and 9).

Example 4

Impact of UPA on Human Mammary Breast Tumor Growth Xenografted into Nude Mice

Material and Methods

The xenograft model used in this study was HBCx-34. HBCx-34 is a mammary ductal carcinoma with wild type P53, no HER2 overexpression and PR and ERα overexpression. The tumor is highly responsive to adriamycine/cyclophosphamide and responsive to docetaxel and capecitabine. HBCx-34 has got no cachectic property.

Tumorgraft Model Induction: Pretreatment Procedures

HBCx-34 tumors (P14.0.0/2) were transplanted subcutaneously onto 5-10 mice (donor mice, passage (n-1), female athymic nude mice (Hsd:Athymic Nude-Fox1nu), 6- to 9-week-old, Harlan Laboratories (Gannat, France)). When these tumors reached 1000 to 2000 mm3 (between 60 to 78 days), donor mice were sacrificed by cervical dislocation, tumors were aseptically excised and dissected. After removing necrotic areas, tumors were cut into fragments measuring approximately 20 mm3 and transferred for 10 min maximum in sterile DMEM/F12 culture medium, without any additional components, before grafting.

Healthy mice aged 6 to 9 weeks and weighing at least 20 g were included in the study. Mice were anaesthetized with ketamine/xylazine, and then skin was aseptized with a chlorhexidine solution, incised at the level of the interscapular region, and a 20 mm3 tumor fragment was placed in the subcutaneous tissue. Skin was closed with clips.

Tumorgraft Model Induction: Treatment Phase

Mice were allocated to different groups according to their tumor volume to give homogenous mean and median tumor volume in each treatment arms. Ten mice/group, with HBCx-34 tumors between 75 and 144 mm³, were randomized according to their tumor volume into experimental groups, and treatments (UPA 130 mg/kg, p.o. or control vehicle) were initiated 33 days post implantation of the tumor for a total duration of 42 days.

Analyses

Mice were observed for physical appearance, behavior and clinical changes. Animals were weighted biweekly during all the experimental period. Toxicity of the different treatments was determined as body weight loss.

Tumor volume was evaluated biweekly during all the experimental period. Tumors were collected at the end of treatment, weight and processed for analysis.

Results

UPA treatment was well tolerated and no significant body weight loss was recorded during the study. No treatment related clinical observation was reported during the experimental period.

Mean tumor volumes (TV) at initiation of treatment were 112.2±7.1 and 102.4±7.7 mm³ in control and UPA-treated groups respectively.

At the end of treatment, a 4.63-fold increase in tumor volume was measured in the control group, with a mean tumor volume of 625.0±108.6 mm³.

UPA exerted an antitumor activity; the mean TV was increased 2.17-fold in the UPA treated mice (mean TV at sacrifice: 332.0±61.0 mm³). The ratio of TV in treated vs. control group (T/C) was 53%.

The invention claimed is:

1. A method for providing regular contraception in a woman who has a family history of breast cancer and/or carries at least one mutation in BRCA 1 gene and/or BRC2 gene, the method comprising administering uilpristal or a metabolite thereof to the woman, wherein the metabolite is selected from the group consisting of CDB-3877, CDB-3963, CDB-3236 and CDB-4183.

2. The method of claim 1, wherein the woman does not suffer from breast cancer.

3. The method of claim 1, wherein ulipristal acetate or the metabolite thereof is administered orally.

4. The method of claim 1, wherein ulipristal acetate or the metabolite thereof is administered by the vaginal or intrauterine route.

5. The method of claim 1, wherein ulipristal acetate or a metabolite thereof is administered daily.

6. The method of claim 1 wherein ulipristal acetate ora metabolite is administered at a dosage from 5 to 80 mg.

7. The method of claim 1, wherein ulipristal acetate or a metabolite thereof is administered at a dosage from 10 to 50 mg.

8. The method of claim 1, wherein ulipristal acetate or a metabolite thereof is administered for at least 3 months.

9. The method of claim 1, wherein the method is further for reducing the risk of developing breast cancer in said woman.

10. The method of claim 9, wherein the woman carries at least onemutation in BRCA1 gene and/or BRCA2 gene.

11. The method of claim 1, wherein the method is further to exert an anti-proliferative effect on non-cancerous breast cell carrying a mutation in BRCA1 and/or BRCA2 gene in said woman, wherein the woman carries at least one mutation in BRCA1 gene and/or BRCA2 gene.

12. The method of claim 11, wherein ulipristal acetate is administered daily at a dosage ranging from 5 mg to 50 mg.

13. A method for inhibiting proliferation of non-cancerous breast cells carrying at least one mutation in BRCA1 and/or BRCA2 gene in a woman, comprising administering ulipristal acetate or a metabolite thereof to the woman.

14. The method of claim 13, which is further for providing contraception in the woman.

15. The method of claim 14, wherein the woman does not suffer from breast cancer.

* * * * *